United States Patent [19]

Nakagawa

[11] Patent Number: 5,425,933
[45] Date of Patent: Jun. 20, 1995

[54] METHOD FOR PREPARING CRYSTALLINE MATERIALS USING HETEROBRIDGED AZA-POLYCYCLIC TEMPLATING AGENTS

[75] Inventor: Yumi Nakagawa, Oakland, Calif.

[73] Assignee: Chevron Research and Technology Company, A Division of Chevron U.S.A. Inc., San Francisco, Calif.

[21] Appl. No.: 193,375

[22] Filed: Feb. 8, 1994

Related U.S. Application Data

[63] Continuation-in-part of Ser. No. 907,419, Jun. 30, 1992, Pat. No. 5,281,407.

[51] Int. Cl.$^6$ .............................................. C01B 39/04
[52] U.S. Cl. ..................... 423/706; 423/708; 423/DIG. 22; 423/DIG. 33; 423/DIG. 36; 502/62
[58] Field of Search ............... 423/706, 708, DIG. 33, 423/DIG. 36, DIG. 22; 502/71, 62

[56] References Cited

U.S. PATENT DOCUMENTS

| | | | |
|---|---|---|---|
| 3,140,249 | 7/1964 | Plank et al. | 208/120 |
| 3,140,251 | 7/1964 | Plank et al. | 208/120 |
| 3,140,253 | 7/1964 | Plank et al. | 208/120 |
| 4,508,837 | 10/1985 | Zones | 502/62 |
| 4,544,538 | 9/1985 | Zones | 423/706 |
| 4,610,854 | 9/1986 | Zones | 423/706 |
| 4,826,667 | 5/1989 | Zones et al. | 423/706 |
| 4,910,006 | 3/1990 | Zones et al. | 423/706 |
| 4,963,337 | 10/1990 | Zones | 423/706 X |
| 5,106,801 | 4/1992 | Zones et al. | 502/64 |
| 5,106,801 | 4/1992 | Zones et al. | 502/64 |
| 5,225,179 | 7/1993 | Zones et al. | 423/709 |
| 5,254,514 | 10/1993 | Nakagawa | 502/62 |
| 5,271,922 | 12/1993 | Nakagawa | 423/702 |
| 5,281,407 | 1/1994 | Nakagawa | 423/706 |

FOREIGN PATENT DOCUMENTS 0400016 11/1981 European Pat. Off. .
0193282 9/1986 European Pat. Off. .

OTHER PUBLICATIONS

Lok et al "The Role of Organic Molecules in Molecular Sieve Synthesis" *Zeolites* Oct. 1983 pp. 282–291.
Helvetica Chimica Acta-vol. 57, FASC. 6 (1974)-NR. 168-169-169. "Formation and Properties of LOSOD, A New Sodium Zeolite" pp. 1533–1549; W. Sieber et al. (no month).

*Primary Examiner*—Karl Group
*Assistant Examiner*—David Sample
*Attorney, Agent, or Firm*—W. K. Turner; R. J. Sheridan

[57] ABSTRACT

Molecular sieves, particularly zeolites, are prepared using heterobridged aza-polycyclic templates. The templates may be prepared in a series of reaction steps which include a Diels-Alder reaction between a diene and a dienophile.

32 Claims, No Drawings

METHOD FOR PREPARING CRYSTALLINE MATERIALS USING HETEROBRIDGED AZA-POLYCYCLIC TEMPLATING AGENTS

This application is a continuation-in-part of Ser. No. 07/907,419, filed Jun. 30, 1992 now U.S. Pat. No. 5,281,407.

BACKGROUND OF THE INVENTION

1. Field of the Invention

The present invention relates to a new method for synthesizing crystalline molecular sieves using a new family of templating agents.

2. Background

The crystalline materials of this invention contain metallic and non-metallic oxides bonded through oxygen linkages to form a three-dimensional structure. Molecular sieves are a commercially important class of crystalline materials. Natural and synthetic crystalline molecular sieves are useful as catalysts and adsorbents. They have distinct crystal structures with ordered pore structures which are demonstrated by distinct X-ray diffraction patterns. The crystal structure defines cavities and pores which are characteristic of the different species. The adsorptive and catalytic properties of each molecular sieve are determined in part by the dimensions of its pores and cavities. Thus, the utility of a particular molecular sieve in a particular application depends at least partly on its crystal structure.

The term "molecular sieve" refers to a material prepared according to the present invention having a fixed, open-network structure, usually crystalline, that may be used to separate hydrocarbons or other mixtures by selective occlusion of one or more of the constituents, or may be used as a catalyst in a catalytic conversion process.

The term "zeolite" refers to a molecular sieve containing a silicate lattice, usually in association with some alumina, boron, gallium, iron, and/or titanium. In the following discussion, the terms molecular sieve and zeolite will be used more or less interchangeably, since most of the work was carried out on zeolites. However, one skilled in the art will recognize that the teachings relating to zeolites are also applicable to the more general class of materials called molecular sieves.

The term "aluminosilicate" refers to a zeolite containing both framework alumina and framework silica. The term "silicate" refers to a zeolite having a high $SiO_2/Al_2O_3$ mole ratio, preferably a $SiO_2/Al_2O_3$ mole ratio greater than 100. The term "borosilicate" refers to a zeolite containing both boron and silicon, and having a $SiO_2/B_2O_3$ ratio of greater than 20.

Organic templating agents are believed to play an important role in the process of molecular sieve crystallization. Organic amines and quaternary ammonium cations were first used in the synthesis of zeolites in the early 1960's. This approach led to a significant increase in the number of new zeolitic structures discovered as well as an expansion in the boundaries of composition of the resultant crystalline products. Previously, products with low silica to alumina ratios ($SiO_2/Al_2O_3 \leq 10$) had been obtained, but upon using the organocations as components in the starting gels, zeolites with increasingly high $SiO_2/Al_2O_3$ ratios were realized.

Crystalline aluminosilicates are usually prepared from aqueous reaction mixtures containing alkali or alkaline earth metal oxides, silica, and alumina. By varying the synthesis conditions and the composition of the reaction mixture, different zeolites can be formed using the same templating agent.

Compounds having chemical structures which fall outside the scope of the present invention have also been disclosed as templating agents for various crystalline materials. Use of N,N,N-trimethyl cyclopentylammonium iodide in the preparation of Zeolite SSZ-15 molecular sieve is disclosed in U.S. Pat. No. 4,610,854; use of 1-azoniaspiro [4.4] nonyl bromide and preparation of a molecular sieve termed "Losod" is disclosed in Hel. Chim. Acta (1974), Vol. 57, page 1533 (W. Sieber and W. M. Meier); use of 1,ω-di(1-azoniabicyclo [2.2.2.] octane) lower alkyl compounds in the preparation of Zeolite SSZ-16 molecular sieve is disclosed in U.S. Pat. No. 4,508,837; use of N,N,N-trialkyl-1 adamantammonium salts in the preparation of zeolite SSZ-13 molecular sieve is disclosed in U.S. Pat. No. 4,544,538. U.S. Pat. No. 5,053,373 discloses preparing SSZ-32 with an N-lower alkyl-N'-isopropyl-imidazolium cation templating agent. U.S. Pat. No. 5,106,801 discloses a cyclic quaternary ammonium ion, and specifically a tricyclodecane quaternary ammonium ion, for the preparation of the metallosilicate zeolite SSZ-31. U.S. Pat. No. 4,910,006 teaches using a hexamethyl[4.3.3.0] propellane-8,11-diammonium cation for the preparation of SSZ-26. EP 0193282 discloses a tropinium cation for preparing the clathrasil ZSM-S8. Similarly, use of quinuclidinium compounds to prepare a zeolite termed "NU-3" is disclosed in European Patent Publication No. 40016. Use of aza-polycyclic templates to prepare molecular sieves is disclosed in copending U.S. Pat. Application No. 907,419, filed Jun. 30, 1992, entitled "METHOD FOR PREPARING. CRYSTALLINE MATERIALS USING AZA-POLYCYCLIC TEMPLATING AGENTS."

SUMMARY OF THE INVENTION

This invention provides a novel process for preparing crystalline materials, and more specifically crystalline oxide materials. This process includes contacting active sources of the components of the crystalline materials and an organocationic templating agent.

More specifically, a method is provided for preparing a crystalline material comprising one or a combination of oxides selected from the group consisting of one or more trivalent element(s) and one or more tetravalent element(s), said method comprising contacting under crystallization conditions sources of said oxides and a heterobridged aza-polycyclic templating agent having a molecular structure of the form:

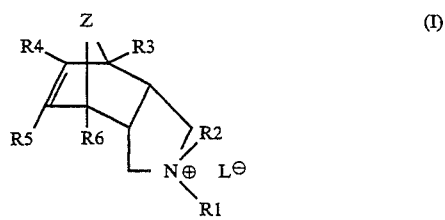

(I)

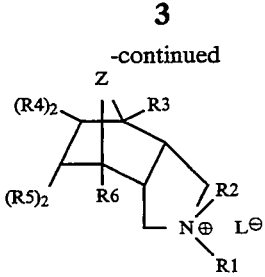

wherein:

Z is oxygen, nitrogen or sulfur;

R1 and R2 are at each independent occurrence selected from the group consisting of hydrogen, a lower alkyl group, and, when taken together, a spirocyclic group having from 3 to 6 carbon atoms;

R3, R4, R5 and R6 are at each independent occurrence selected from the group consisting of hydrogen, halogen, and a lower alkyl group; and L is an anion which is not detrimental to the formation of the crystalline material.

The aza-polycyclic compounds encompassed by these formulas have a charged nitrogen heteroatom and a bridging structure containing a hetero atom and forming a multiplicity of rings. These compounds are hereinafter referred to as the "defined heterobridged aza-polycyclic templating agents".

The preferred crystalline material is a molecular sieve. The preferred trivalent element is selected from the group consisting of aluminum, boron, gallium, iron, and combinations thereof, with aluminum and/or boron being particularly preferred. The preferred tetravalent element is selected from silicon and germanium, with silicon being particularly preferred.

The present invention is also directed to a crystalline material comprising tetrahedrally bound oxide units and the defined heterobridged aza-polycyclic templating agent, said oxide units comprising one or a combination of trivalent elements and tetravalent elements.

Preferably, the composition comprising oxide units has a molar composition, as synthesized and in the anhydrous state, as follows:

| As-synthesized Composition | | |
|---|---|---|
| | Broad | Preferred |
| $YO_2/W_2O_3$ | 30 or greater | 50 or greater |
| $Q/YO_2$ | 0.01–0.10 | 0.02–0.07 |
| $M^+/YO_2$ | less than 0.05 | less than 0.03 | wherein:

Q is the defined heterobridged aza-polycyclic templating agent having a molecular structure of the form shown in Formulas I and II above;

M is one or a combination of alkali metal cations and/or alkaline earth metal cations;

W is one or a combination of elements selected from aluminum, boron, gallium, and iron; and Y is one or a combination of elements selected from silicon and germanium.

Among other factors, the present invention is based on the discovery that small changes in structure within this family of relatively rigid, polycyclic templating agents, when the template is used in molecular sieve synthesis, can lead to significant changes in the crystalline molecular sieve formed. In particular, this family of templates can be used to make several catalytically interesting large-pore zeolites under a variety of reaction conditions.

DETAILED DESCRIPTION OF THE INVENTION

In preparing a crystalline material according to the present invention, a defined heterobridged aza-polycyclic compound, having a general molecular structure of the form shown in Formulas I and II above, acts as a template or structure directing agent during the crystallization.

Crystalline zeolites which may be prepared according to the present process include MTW (ZSM-12), ZSM-48, EUO, ZSM-5 and other similar materials. New crystalline molecular sieve structures may result as well by the present method.

In the method of this invention the family of defined heterobridged aza-polycyclic templates can be used to synthesize different zeolitic materials depending on the reagents, reactant ratios and reaction conditions. For example, factors which may affect the crystallization of a given zeolite include the specific defined heterobridged aza-polycyclic template used, the type and ratio of inorganic reagents used, the concentration of alkali metal relative to the metal oxide concentrations, temperature, and time.

The full scope of the composition and process of the present invention will be apparent to those familiar with crystalline molecular sieves and their methods of preparation from the following detailed description of the principal features of the composition and from the examples which accompany the description.

Templating Agent

The templating agents useful in the present process have a molecular structure of the general form:

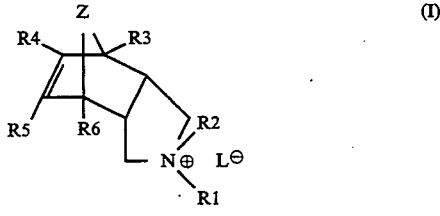

(I)

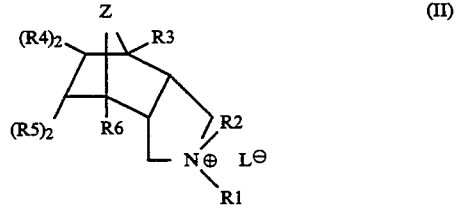

(II)

wherein:

Z is oxygen, nitrogen or sulfur;

R1 and R2 are at each independent occurrence selected from the group consisting of hydrogen, a lower alkyl group, and, when taken together, a spirocyclic group having from 3 to 6 carbon atoms;

R3, R4, R5 and R6 are at each independent occurrence selected from the group consisting of hydrogen, halogen, and a lower alkyl group; and L is an anion which is not detrimental to the formation of the crystalline material.

As used herein, the term "halogen" refers to fluorine, chlorine, bromine, and combinations thereof. The term "lower alkyl group" refers to a linear, branched, or cyclic alkyl group having from 1 to 6 carbon atoms. The term "spirocyclic group" refers to a cyclic group in a polycyclic hydrocarbon having one carbon atom in common with a second cyclic group.

L is an anion which is not detrimental to the formation of the molecular sieve. Representative anions include halogens, such as fluoride, chloride, bromide, and iodide, hydroxide, acetate, sulfate, carboxylate. Hydroxide is the most preferred anion. It may be beneficial to ion exchange, for example, an hydroxide ion for the halide ion, thereby reducing or eliminating the alkali metal hydroxide quantity required.

Preferably, Z is oxygen. R1 and R2 are preferably each selected from the group consisting of hydrogen, an alkyl group having from 1 to 3 carbon atoms, and, when taken together, a spirocyclic group having from 3 to 6, more preferably from 4 to 5, carbon atoms.

Preferably, R3, R4, R5 and R6 are each selected from the group consisting of hydrogen, halogen, and an alkyl group having from 1 to 3 carbon atoms.

In particular, each member of the family has a charged nitrogen heteroatom and a bridging structure containing a hetero atom and forming a multiplicity of rings.

Many of the organocations which have been previously used as templates for molecular sieve synthesis are conformationally flexible. These molecules adopt many conformations in aqueous solution, and several templates can give rise to a single crystalline product. In contrast, the defined heterobridged aza-polycyclic templating agents used in the present invention are conformationally rigid organic molecules. Altering the structure of these rigid molecules can lead to a change in the molecular sieve obtained, presumably due to the differing steric demands of each template. In particular, it has been found that the present templating agents are useful for synthesizing large pore zeolites, which are important for catalytic applications.

However, increasing the steric demand of the template may lead to a decrease in crystallization rate as well as a decrease in template solubility in the reaction mixture. If the template is not sufficiently soluble, it will be difficult to form crystals in the reaction mixture.

Addition of a surfactant to the reaction mixture may help to solubilize the template.

Employing a Diels-Alder reaction scheme, using inexpensive reagents, is the preferred method for preparing the present templating agents. The Diels-Alder reaction is one of the most useful transformations in synthetic organic chemistry. Two new bonds and a six-membered ring are formed in the Diels-Alder reaction, formally a [4+2] cycloaddition of a 1,4-conjugated diene with a double bond (dienophile). The dienophile may include a carbon-carbon, carbon-heteroatom, or heteroatom-heteroatom double (or triple) bond, leading to a diverse pool of potential templating agents. Electron-withdrawing groups on the dienophile greatly increase its reactivity, whereas electron-donating groups on the diene have the same effect. The Diels-Alder reaction is discussed in greater detail in F. Fringuelli and A. Taticchi, Dienes in the Diels-Alder Reaction 1990, J.Wiley and Sons, Inc.

The versatility of the Diels-Alder reaction is in part responsible for its usefulness. A wide range of starting materials are available, making possible the preparation of numerous products. The stereoelectronics of the reaction, as well as its concerted nature, often allows one to predict which product will be formed if several are possible. Therefore, by the proper choice of starting materials, very efficient syntheses of target templates can be achieved.

In particular, the Diels-Alder reaction pathway provides a method for synthesizing the defined heterobridged aza-polycyclic ring systems which are useful in the present invention. Varying either the diene or the dienophile produces small but significant structural changes to the key intermediates in the synthesis.

The dienes useful for preparing the defined heterobridged aza-polycyclic templates are of the following general form:

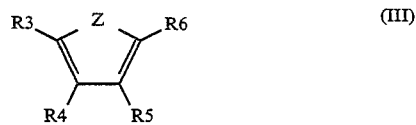

wherein Z, R3, R4, R5 and R6 are as defined above.

Non-limiting examples of heterodienes which are used in preparing the templating agents of this invention include furan, pyrrole, thiophene and derivatives thereof.

The dienophile from which the present templating agent is prepared has a structure of the general form:

wherein X is either oxygen or nitrogen having a substituent group selected from the group consisting of hydrogen and a lower alkyl group.

The defined heterobridged aza-polycyclic compounds are prepared by methods known in the art. The reactions involved are described in detail in, for example, Chem. Pharm. Bull. (1962), 10, 714–718, L. F. Fieser and M. Fieser, 1967, Reagents for Organic Synthesis, vol 1, pp. 581–594, New York: J. Wiley and Sons, Inc. and W. K. Anderson and A. S. Milowsky, 1985, J. Org. Chem. 50,5423–24. When a diene, such as that shown in structure III above, is reacted with a dienophile such as that shown in structure IV, wherein element X is oxygen, the resulting product is reacted with an amine to form an imide, then reduced to the corresponding pyrrolidine using a reducing agent such as lithium aluminum hydride, and then quaternized with, for example methyl iodide, to form the defined heterobridged aza-polycyclic templating agent.

When the diene of structure III above, is reacted with a dienophile of structure IV, wherein element X is nitrogen having a lower alkyl substituent group, the resulting imide product is directly reduced to the corresponding pyrrolidine and then quaternized to form the cationic templating agent.

The double bond shown in Formula I above is not critical to the action of the defined heterobridged aza-polycyclic compound as a templating agent, and may be reduced, using techniques readily available in the art, such as, for example, by reaction over a palladium/carbon or a platinum/carbon catalyst in the presence of hydrogen. The reduced compound, having Formula II above, will also serve as a templating agent in the present method.

Crystalline Materials of this Invention

The crystalline materials of this invention comprise the templating agent in combination with metallic and non-metallic oxides bonded in tetrahedral coordination through shared oxygen atoms to form a cross-linked three dimensional crystal structure. The metallic and non-metallic oxides comprise one or a combination of oxides selected from the group consisting of one or more trivalent element(s) and one or more tetravalent element(s). The trivalent element is preferably selected from the group consisting of aluminum, boron, gallium, iron, and combinations thereof. More preferably, the trivalent element is selected from the group consisting of aluminum and boron. The tetravalent element is selected from the group consisting of silicon, germanium, and combinations thereof. More preferably, the tetravalent element is silicon.

The crystalline material comprises one or a combination of oxides, said oxides being selected from a range of metal oxidation states. The crystalline material also contains a defined heterobridged aza-polycyclic templating agent having the molecular structure of the form shown in Formulas I and II above. The entire lattice is charged balanced.

Preferably, the crystalline material has a molar composition, as synthesized and in the anhydrous state, as follows:

| As-synthesized Composition | | |
|---|---|---|
| | Broad | Preferred |
| $YO_2/W_2O_3$ | 30 or greater | 50 or greater |
| $Q/YO_2$ | 0.01–0.10 | 0.02–0.07 |
| $M^+/YO_2$ | less than 0.05 | less than 0.03 | wherein:
Q is the defined heterobridged aza-polycyclic templating agent having a molecular structure of the form shown in Formulas I and II above;
M is one or a combination of alkali metal cations and/or alkaline earth metal cations;
W is one or a combination of elements selected from aluminum, boron, gallium, and iron; and
Y is one or a combination of elements selected from silicon and germanium.

The crystalline materials can be suitably prepared from an aqueous solution containing sources of at least one templating agent of this invention, and at least one oxide capable of forming a crystalline molecular sieve. Examples of a suitable metal oxide include an alkali metal oxide, and oxides of aluminum, silicon, boron, germanium, iron, gallium, and the like. The reaction mixture should have a composition in terms of mole ratios falling within the following ranges:

| Reaction Mixture Composition | | |
|---|---|---|
| | Broad | Preferred |
| $YO_2/W_2O_3$ | 25 and greater | 35 and greater |
| $OH^-/YO_2$ | 0.10–0.70 | 0.15–0.40 |
| $Q/YO_2$ | 0.05–0.40 | 0.10–0.30 |
| $M^+/YO_2$ | 0.05–0.40 | 0.05–0.20 |
| $H_2O/YO_2$ | 25–100 | 20 to 50 | wherein Y, W, Q and M are as defined above.

The present process is suitable for preparing aluminosilicate zeolites from a reaction mixture prepared using standard zeolitic preparation techniques. Typical sources of aluminum oxide for the reaction mixture include aluminates, alumina, and aluminum compounds such as $AlCl_3$, hydrated $Al(OH)_3$ gels and $Al_2(SO_4)_3$. Typical sources of silicon oxide include silicates, silica hydrogel, silicic acid, colloidal silica, tetra-alkyl orthosilicates, and silica hydroxides. Gallium, germanium, iron, and boron can be added in forms corresponding to their aluminum and silicon counterparts.

Alternatively a source zeolite reagent, such as zeolite A, zeolite X, zeolite Y, and zeolite rho, may provide a source of alumina for the present process. In some cases, the source zeolite may also provide a source of silica and/or boron. Alternatively, the source zeolite in its dealuminated forms may be used as a source of silica, with additional silicon added using, for example, the conventional sources listed above.

Typically, an alkali metal hydroxide and/or an alkaline earth metal hydroxide, such as the hydroxide of sodium, potassium, lithium, cesium, rubidium, calcium, and magnesium, is used in the reaction mixture; however, this component can be omitted so long as the equivalent basicity is maintained. The templating agent may be used to provide hydroxide ion. The alkali metal cation or alkaline earth metal cation may be part of the as-synthesized crystalline oxide material, in order to balance valence electron charges therein.

The present process is suitable for preparing silicates or "essentially alumina-free" zeolites, i.e., a product having a silica to alumina mole ratio of $\infty$. The term "essentially alumina-free" is used because it is difficult to prepare completely aluminum-free reaction mixtures for synthesizing these materials. Especially when commercial silica sources are used, aluminum is almost always present to a greater or lesser degree. The hydrothermal reaction mixtures from which the essentially alumina-free crystalline siliceous molecular sieves may be prepared can be referred to as being substantially alumina free. By this usage is meant that no aluminum is intentionally added to the reaction mixture, e.g., as an alumina or aluminate reagent, and that to the extent aluminum is present, it occurs only as a contaminant in the reagents. An additional method of increasing the mole ratio of silica to alumina is by using standard acid leaching or chelating treatments.

In preparing the crystalline material under crystallization conditions according to the present invention, the reaction mixture is maintained at an elevated temperature until crystals are formed. The temperatures during the hydrothermal crystallization step are typically maintained from about 100° C. to about 235° C., preferably from about 120° C. to about 200° C. The crystallization period is typically greater than 1 day and preferably from about 3 days to about 50 days.

The hydrothermal crystallization is usually conducted under pressure and usually in an autoclave so that the reaction mixture is subject to autogenous pressure. The reaction mixture can be stirred during crystallization.

Once the crystals have formed, the solid product is separated from the reaction mixture by standard mechanical separation techniques, such as filtration. The crystals are water-washed and then dried, e.g., at 90° C. to 150° C. for from 8 to 24 hours, to obtain the synthesized zeolite crystals. The drying step can be performed at atmospheric or subatmospheric pressures.

During the hydrothermal crystallization step, the crystals can be allowed to nucleate spontaneously from the reaction mixture. The reaction mixture can also be seeded with crystals both to direct, and accelerate the crystallization, as well as to minimize the formation of undesired aluminosilicate contaminants. If the reaction mixture is seeded with crystals, the concentration of the defined heterobridged aza-polycyclic template may sometimes be somewhat reduced.

Due to the unpredictability of the factors which control nucleation and crystallization in the art of crystalline oxide synthesis, not every combination of reagents, reactant ratios, and reaction conditions will result in crystalline products. Selecting crystallization conditions which are effective for producing crystals may require routine modifications to the reaction mixture composition or to the reaction conditions, such as temperature and/or crystallization time. Making these modifications are well within the capabilities of one skilled in the art.

The crystalline material, more specifically the synthetic molecular sieve or zeolite, can be thermally treated (calcined). Usually, it is desirable to remove the alkali metal cation by ion exchange and replace it with hydrogen, ammonium, or any desired metal ion. The zeolite can be leached with chelating agents, e.g., EDTA or dilute acid solutions, to increase the silica alumina mole ratio. The zeolite can also be steamed; steaming helps stabilize the crystalline lattice to attack from acids. The zeolite can be used in intimate combination with hydrogenating components, such as tungsten, vanadium molybdenum, rhenium, nickel cobalt, chromium, manganese, or a noble metal, such as palladium or platinum, for those applications in which a hydrogenation-dehydrogenation function is desired. Typical replacing cations can include metal cations, e.g., rare earth, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, and Fe are particularly preferred.

The hydrogen, ammonium, and metal components can be exchanged into the zeolite. The zeolite can also be impregnated with the metals, or, the metals can be physically intimately admixed with the zeolite using standard methods known to the art. The metals can also be occluded in the crystal lattice by having the desired metals present as ions in the reaction mixture from which the zeolite is prepared.

Typical ion exchange techniques involve contacting the synthetic zeolite with a solution containing a salt of the desired replacing cation or cations. Although a wide variety of salts can be employed, chlorides and other halides, nitrates, and sulfates are particularly preferred. Representative ion exchange techniques are disclosed in a wide variety of patents including U.S. Pat. Nos. 3,140,249; 3,140,251; and 3,140,253. Ion exchange can take place therefore before or after the zeolite is calcined.

Following contact with the salt solution of the desired replacing cation, the zeolite is typically washed with water and dried at temperatures ranging from 65° C. to about 315° C. After washing, the zeolite can be calcined in air or inert gas at temperatures ranging from about 200° C. to about 800° C. for periods of time ranging from 1 to 48 hours, or more, to produce a catalytically active product especially useful in hydrocarbon conversion processes.

Regardless of the cations present in the synthesized form of the zeolite, the spatial arrangement of the atoms which form the basic crystal lattice of the zeolite remains essentially unchanged. The exchange of cations has little, if any effect on the zeolite lattice structures.

The molecular sieve can be formed into a wide variety of physical shapes. Generally speaking, the zeolite can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the aluminosilicate can be extruded before drying, or, dried or partially dried and then extruded.

The zeolite can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., which is incorporated by reference herein in its entirety.

The zeolites prepared by the process of this invention are useful as catalysts in hydrocarbon conversion processes such as catalytic cracking, hydrocracking, dewaxing, alkylation, aromatics formation, isomerization and the like.

The following examples demonstrate but do not limit the present invention.

EXAMPLES.

Examples 1–5 show that one can make a wide range of templates using this methodology. In each of examples 1–5, the anion L may be either I− or OH−.

EXAMPLE 1

Synthesis of 4-azonia-4,4-dimethyl-10-oxatricyclo[5.2.1.0$^{2,6}$]dec-8-ene hydroxide (Template A)

A 2-liter, 3-necked flask was equipped with a magnetic stirrer, addition funnel and thermometer and charged with 20.0 grams of N-methylmaleimide and 1000 grams of dimethyl ether. 18.20 Grams of furan were added dropwise, and the reaction mixture was stirred at room temperature for 20 days. The reaction mixture was concentrated to a white solid which was chromatographed on a silica gel column to afford 8.9 grams of the endo-Diels-Alder adduct and 7.6 grams of the exo-Diels-Alder adduct. 6.2 Grams of a mixture of the two isomers was also obtained.

A 250 ml 3-necked flask was charged with 5.9 grams of lithium aluminum hydride (LAH) and 113 ml of anhydrous diethyl ether, and the resulting suspension was cooled to 0° C. 8.8 Grams of the endo-Diels-Alder adduct was dissolved in 56 ml of anhydrous dichloromethane and was added via an addition funnel to the LAH solution at a rate so as to keep the reaction temperature at or below 0° C. Evolution of gas was observed. Following complete addition of the adduct, the cooling bath was removed and the reaction mixture was stirred at room temperature for three days. The LAH was quenched by the careful and slow addition of 5.4 grams of water (CAUTION: very vigorous evolution of gas and exothermic reaction), followed by the addition of 5.4 ml of 15% aqueous NaOH. The volume of ether that was lost through volatilization was replaced with dichloromethane. Another 16.2 ml of water was added, and the grey reaction mixture turned white and was stirred at room temperature for 30 minutes. The solids were removed by filtration and washed thoroughly with dichloromethane. The filtrate was transferred to a separatory funnel, 50 ml of water was added and the pH of the aqueous layer was adjusted to $\leq 2$ with concentrated HCl. The phases were separated and the acid wash was repeated. The pH of the combined aqueous phases was adjusted to $\geq 12$ using 50% aqueous NaOH, and this layer was extracted three times with 50 ml of EtOAc. The combined organic extracts were dried over $Na_2SO_4$, filtered and concentrated to yield 6.7 grams of the desired endo-N-methylpyrrolidine derivative.

The pyrrolidine derivative (6.64 grams) was dissolved in 44 ml of $CHCl_3$ in a round-bottomed flask and 12.6 grams of methyl iodide were added dropwise. The resulting heterogeneous mixture was stirred at room temperature for ten days. Ether was then added to the reaction mixture to promote further precipitation of the product, and the solids were collected by filtration. Recrystallization from hot acetone/methanol/ether afforded 8.9 grams of the desired endo-4-azonia-4,4-dimethyl-10-oxa-tricyclo[5.2.1.0$^{2,6}$] dec-8-ene iodide.

The iodide salt was converted to the hydroxide form using Bio-Rad AG1-X8 anion exchange resin.

EXAMPLE 2

Synthesis of exo-4-azonia-4,4-dimethyl-10-oxatricyclo[5.2.1.0$^{2,6}$]dec-8-ene hydroxide (Template B)

79.10 Grams of exo-3,6-epoxy-1,2,3,6-tetrahydrophthalic anhydride and 1640 mls of 40% aqueous methylamine were added to a 2-liter, 3-necked flask. 11.75 Grams of 4-dimethylaminopyridine were added dropwise to the stirring solution and the reaction mixture was stirred for an additional two hours at room temperature, after which it was heated at 70° C. for two days. The dimethylamine was removed by heating to 100° C., then the solution was cooled to 0° C. and acidified (pH $\leq 2$) with concentrated HCl. The aqueous solution was transferred to a separatory funnel and washed twice with EtOAc. The organic extracts were combined, dried over $MgSO_4$, filtered and concentrated. The aqueous phase was extracted twice with $CH_2Cl_2$ and twice with EtOAc. The combined organic phases were also dried over $MgSO_4$, filtered and concentrated. The total yield of the desired exo-Diels-Alder adduct was 12.5 grams. Reduction of the exo-adduct was performed as described in Example 1 for the endo-adduct. Similarly, quaternarization with methyl iodide and anion exchange with Bio-Rad AG1-X8 resin were performed as described in Example 1 to yield exo-4-azonia-4,4-dimethyl-10-oxa-tricyclo[5.2.1.0$^{2,6}$]dec-8-ene hydroxide (Template B).

EXAMPLE 3

Synthesis of endo-4-azonia-1,4,4,7-tetramethyl-10-oxa-tricyclo[5.2.1.0$^{2,6}$]dec-8-ene hydroxide (Template C)

A 1-liter flask was charged with 50.0 grams of N-methylmaleimide and 450 ml of $CHCl_3$. 46.6 Grams of 2,5-dimethylfuran was added dropwise and the reaction mixture was heated to reflux and monitored for the disappearance of the starting material. After 14 days, starting material was still apparent, but the reaction mixture was washed twice with 1N NaOH. The organic layer was dried over $MgSO_4$, filtered and concentrated to yield 94 grams of crude solid material. 50.0 Grams of this solid was chromatographed on a silica gel column to yield 18.0 grams of exo-Diels-Alder adduct and 4.3 grams of the endo-adduct.

Reduction of each isomer with LAH, quaternarization and anion exchange were performed as described in Example 1 to afford endo-4-azonia-1,4,4,7-tetramethyl-10-oxatricyclo[5.2.1.0$^{2,6}$]dec-8-ene hydroxide (Template C) and the corresponding endo isomer (Template D).

EXAMPLE 4

Synthesis of Template E

The procedure for synthesizing Template C was repeated, except that ethyl iodide was used instead of methyl iodide in the quaternarization step.

EXAMPLE 5

Synthesis of Template F

24 Grams of 7-oxabicyclo[2.2.1]heptane-2,3-dicarboxylic anhydride, 61.4 mls of 40% aqueous methylamine, and 3.5 grams of 4-dimethylaminopyridine were mixed in a 250 ml round-bottomed flak. The contents of the flask was divided and poured into two Teflon liners for 125 ml Parr reactors, and the reactors were sealed and heated at 90° C. for 24 hours. The resultant mixtures were combined and cooled to 0° C. in an ice bath and the pH was adjusted to $\leq 2$ with concentrated HCl. This solution was extracted three times with $CHCl_2$, and the combined organic phases were dried over $MgSO_4$, filtered and concentrated to yield 12.75 grams of the crude Diels-Alder adduct as a white solid.

The adduct was reduced to the corresponding methylpyrrolidone derivative using LAH as described in Example 1. Quaternarization with methyl iodide and anion exchange were also performed as described in Example 1.

Examples 6-18 illustrate using templates of this invention under a variety of inorganic conditions to obtain zeolitic products. These non-limiting examples illustrate preferred conditions of the invention.

EXAMPLE 6

Preparation of Zeolite ZSM-48

3.86 Grams of a 0.527M solution of Template D as the hydroxide salt, 3.6 grams of water, and 0.5 gram of 1.0N NaOH solution were mixed in a Teflon cup for a Parr 4745 reactor. 0.62 Gram of Cabosil M-5 colloidal silica was then added to the mixture and the resulting mixture was stirred until homogeneous. The reaction mixture was heated at 160° C. for 21 days, after which a settled product was obtained. The product was collected by filtration, washed with distilled water and dried. Analysis by X-ray diffraction (XRD) indicated that the product was ZSM-48.

EXAMPLE 7

Preparation of Zeolite MTW 4.27 Grams of a 0.527M solution of Template D as the hydroxide salt, 1.58 grams of water, 1.43 grams of a 1.0N NaOH solution and 0.057 gram of sodium borate decahydrate were mixed in a Teflon cup for a Parr 4745 reactor. 0.92 Gram of Cabosil M-5 colloidal silica was then added and the resulting mixture was stirred until homogeneous. This reaction mixture was heated to 160° C. and tumbled at 43 rpm on a rotating spit in a Blue M oven. After 13 days, a product was obtained which was determined by XRD to be MTW.

EXAMPLE 8

Preparation of Zeolite MTW

The procedure described in Example 7 was repeated, except that 3.80 grams of a 0.59M solution of Template B was used instead of Template D. After seven days, a settled product was obtained which was determined by XRD to be MTW.

EXAMPLE 9

Preparation of Zeolite (Al)MTW 5.07 Grams of a 0.59M solution of Template B as the hydroxide salt, 4.97 grams of water, 0.75 gram of 1.0N KOH solution and 0.015 gram of Reheis F2000 (hydrated aluminum hydroxide) were mixed in a Teflon cup of a Parr 4745 reactor. 0.62 Gram of Cabosil M-5 colloidal silica was then added and the resulting mixture was stirred until homogeneous. The reaction mixture was heated to 160° C. and tumbled at 43 rpm on a rotating spit in a Blue M oven. After 24 days, a product was obtained which was identified by XRD as being MTW.

EXAMPLE 10

Preparation of Zeolite ZSM-48

3.73 Grams of a 0.60M solution of Template C as the hydroxide salt, 6.66 grams of water, 1.5 grams of 1.0N KOH solution and 0.92 gram of Cabosil M-5 colloidal silica were mixed together until a homogeneous solution formed. This reaction mixture was heated to 160° C. and, after 18 days, a settled product was obtained. The product was identified by XRD as ZSM-48 with a small amount of layered material.

EXAMPLE 11

Preparation of Zeolite MTW

The procedure described in Example 7 was repeated, except that 3.73 grams of a 0.60M solution of Template C was used instead of Template D. After 15 days, a product was obtained which was determined by XRD to be MTW.

EXAMPLE 12

Preparation of Zeolite (Al)MTW

The procedure described in Example 9 was repeated, except that 3.73 grams of a 0.60M solution of Template C was used instead of Template B. After 37 days, a settled product was obtained which was determined by XRD to be MTW.

EXAMPLE 13

Preparation of Zeolite ZSM-48 +MTW 3.08 Grams of a 0.65M solution of Template F as the hydroxide salt, 0.5 gram of 1.0N KOH solution, 4.33 grams of water and 0.62 gram of Cabosil M-5 colloidal silica were mixed together until a homogeneous solution formed. This reaction mixture was heated at 160° C. for 13 days and the product obtained was determined by XRD to be ZSM-48 with a minor amount of MTW.

EXAMPLE 14

Preparation of Zeolite MTW

The procedure of Example 7 was repeated, except that 3.46 grams of a 0.65M solution of Template F as the hydroxide salt was used instead of Template D. After seven days, a settled product was obtained and determined to be MTW.

EXAMPLE 15

Preparation of Zeolite EUO

The procedure of Example 9 was repeated, except that 3.46 grams of a 0.65M solution of Template F as the hydroxide salt was used instead of Template B. After 13 days, a settled product was obtained which was determined by XRD to be EUO.

EXAMPLE 16

Preparation of Zeolite MTW 2.84 Grams of a 0.53M solution of Template A as the hydroxide salt, 3.86 grams of water, 1.31 grams of a 1.0N NaOH solution and 0.384 gram of sodium borate decahydrate were mixed until homogeneous. 0.62 Grams of Cabosil M-5 colloidal silica was then added and the resulting mixture was heated at 160° C. and tumbled at 43 rpm. After 14 days, a settled product was obtained which was determined by XRD to be MTW.

EXAMPLE 17

Preparation of ZSM-48

The procedure of Example 6 was repeated, except that 2.84 grams of a 0.53M solution of Template A as the hydroxide salt was used instead of Template D. After 14 days at 150° C., a product was obtained which was determined by XRD to be ZSM-48.

EXAMPLE 18

Preparation of Zeolite MTW

The procedure of Example 7 was repeated, except that 3.85 grams of a 0.58M solution of Template E as the hydroxide salt was used instead of Template D. After heating for 13 days, a settled product was obtained which was determined by XRD to be MTW.

It can be seen that one of the desirable features of this invention is that a variety of large pore zeolites can be prepared. As is the case in most molecular sieve syntheses, a given template may not necessarily produce a crystalline product or a single molecular sieve over all inorganic composition ranges.

What is claimed is:

1. A method of preparing a crystalline material comprising one or a combination of oxides selected from the group consisting of one or more trivalent element(s) and one or more tetravalent element(s), said method comprising contacting under crystallization conditions sources of said oxides and a templating agent having a molecular structure of the form:

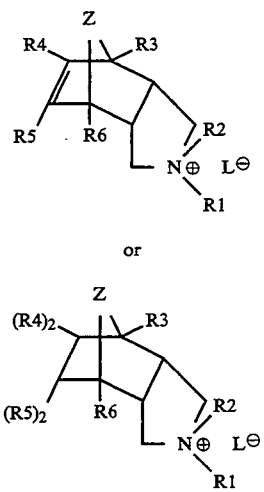

wherein:
  Z is oxygen, nitrogen or sulfur;
  R1 and R2 are at each independent occurrence selected from the group consisting of hydrogen, a lower alkyl group, and, when taken together, a spirocyclic group having from 3 to 6 carbon atoms;
  R3, R4, R5 and R6 are at each independent occurrence selected from the group consisting of hydrogen, halogen, and a lower alkyl group; and
  L is an anion which is not detrimental to the formation of the crystalline material.

2. The method according to claim 1 wherein Z is oxygen.

3. The method according to claim 1 wherein halogen of R3, R4, R5 and R6 is selected from the group consisting of fluorine, chlorine, bromine and combinations thereof.

4. The method according to claim 1 wherein R1 and R2 are each selected from the group consisting of hydrogen, an alkyl group having from 1 to 3 carbon atoms, and, when taken together, a spirocyclic group having from 4 to 5 carbon atoms.

5. The method according to claim 1 wherein R3, R4, R5 and R6 are each selected from the group consisting of hydrogen and an alkyl group having from 1 to 3 carbon atoms.

6. The method according to claim 1 wherein L is selected from the group consisting of fluoride, chloride, bromide, iodide, hydroxide, acetate, sulfate, and carboxylate.

7. The method according to claim 6 wherein L is hydroxide.

8. The method according to claim 1 wherein the trivalent element is selected from the group consisting of aluminum, boron, gallium, iron, and combinations thereof.

9. The method according to claim 8 wherein the trivalent element is selected from the group consisting of aluminum, boron, and combinations thereof.

10. The method according to claim 1 wherein the tetravalent element is selected from the group consisting of silicon, germanium, and combinations thereof.

11. The method according to claim 10 wherein the tetravalent element is silicon.

12. The method according to claim 1 wherein the crystalline material is a molecular sieve.

13. The method according to claim 12 wherein the molecular sieve is a crystalline silicate.

14. The method according to claim 12 wherein the molecular sieve is a crystalline borosilicate.

15. The method according to claim 12 wherein the molecular sieve is a crystalline aluminosilicate zeolite.

16. The method according to claim 12 wherein the molecular sieve is MTW.

17. The method according to claim 12 wherein the molecular sieve is ZSM-48.

18. The method according to claim 12 wherein the molecular sieve is EUO.

19. The method according to claim 12 wherein the molecular sieve is ZSM-5.

20. A crystalline material comprising one or a combination of oxides selected from the group consisting of one or more trivalent element(s) and one or more tetravalent element(s), and having therein the templating agent having a molecular structure of the form:

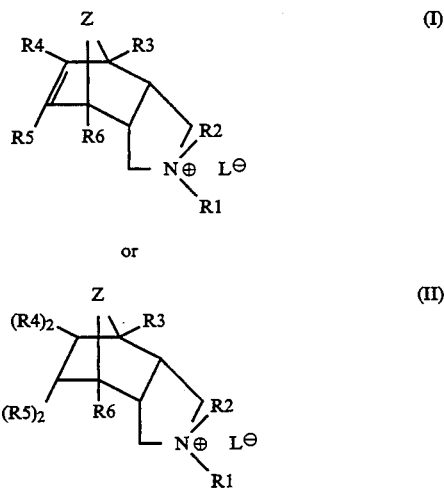

wherein:
  Z is oxygen, nitrogen or sulfur;
  R1 and R2 are at each independent occurrence selected from the group consisting of hydrogen, a lower alkyl group, and, when taken together, a spirocyclic group having from 3 to 6 carbon atoms;
  R3, R4, R5 and R6 are at each independent occurrence selected from the group consisting of hydrogen, halogen, and a lower alkyl group; and
  L is an anion which is not detrimental to the formation of the crystalline material.

21. The crystalline material of claim 20 comprising oxide units and having a molar composition, as synthesized and in the anhydrous state, as follows:

| | |
|---|---|
| $YO_2/W_2O_3$ | 30 or greater |
| $Q/YO_2$ | 0.01–0.10 |
| $M^+/YO_2$ | less than 0.05 | wherein:
  Q is the templating agent;
  M is one or a combination of alkali metal cations and/or alkaline earth metal cations;
  W is one or a combination of elements selected from aluminum, boron, gallium, and iron; and
  Y is one or a combination of elements selected from silicon and germanium.

22. The crystalline material of claim 21 wherein:

| | |
|---|---|
| $YO_2/W_2O_3$ | 50 or greater |
| $Q/YO_2$ | 0.02–0.07 |
| $M^+/YO_2$ | less than 0.03 |

23. The composition according to claim 21 wherein the crystalline material is a molecular sieve.

24. The composition according to claim 23 wherein the molecular sieve is a silicate zeolite.

25. The composition according to claim 23 wherein the molecular sieve is a borosilicate zeolite.

26. The composition according to claim 23 wherein the molecular sieve is an aluminosilicate zeolite.

27. The composition according to claim 22 wherein the crystalline material is a molecular sieve.

28. The composition according to claim 27 wherein the molecular sieve is a silicate zeolite.

29. The composition according to claim 27 wherein the molecular sieve is a borosilicate zeolite.

30. The composition according to claim 27 wherein the molecular sieve is an aluminosilicate zeolite.

31. The process of thermally treating the crystalline material of claim 20 at a temperature of about 200° C. to about 800° C.

32. The process of thermally treating the crystalline material of claim 21 at a temperature of about 200° C. to about 800° C.

* * * * *